United States Patent [19]

Cragoe, Jr. et al.

[11] 4,431,660

[45] Feb. 14, 1984

[54] (4'-BIPHENYLYLOXY AND-THIO-OXY)-3-HYDROXY-3-PYRROLINE-2,5-DIONES AND A METHOD OF TREATING CALCIUM OXALATE RENAL LITHIASIS THEREWITH

[75] Inventors: Edward J. Cragoe, Jr., Lansdale; Clarence S. Rooney, Worcester, both of Pa.; Haydn W. R. Williams, Dollard des Ormeaux, Canada

[73] Assignee: Merck & Co., Inc., Rahway, N.Y.

[21] Appl. No.: 197,854

[22] Filed: Oct. 17, 1980

Related U.S. Application Data

[62] Division of Ser. No. 47,413, Jun. 11, 1979, Pat. No. 4,256,758.

[51] Int. Cl.$^3$ .................. C07D 207/456; A61K 31/40
[52] U.S. Cl. ...................................... 424/274; 548/548
[58] Field of Search ............. 260/326.5 FM; 424/274; 548/548

*Primary Examiner*—Donald G. Daus
*Assistant Examiner*—W. B. Springer
*Attorney, Agent, or Firm*—Theresa Y. Cheng; Thomas E. Arther

[57] ABSTRACT

Novel 4-substituted-3-hydroxy-3-pyrroline-2,5-diones are disclosed which inhibit glycolic acid oxidase and thus are useful in the treatment and prevention of calcium oxalate renal lithiasis.

5 Claims, No Drawings

(4'-BIPHENYLYLOXY AND-THIO-OXY)-3-HYDROXY-3-PYRROLINE-2,5-DIONES AND A METHOD OF TREATING CALCIUM OXALATE RENAL LITHIASIS THEREWITH

This is a division of application Ser. No. 47,413 filed June 11, 1979, now U.S. Pat. No. 4,256,758.

BACKGROUND OF THE INVENTION

Close to 70% of kidney stones in man are composed partially or predominantly of calcium oxalate. There is no satisfactory drug therapy specific for the treatment of calcium oxalate renal lithiasis, nor for prophylactic use by patients prone to recurrent attacks of this disease.

The most common treatment for renal lithiasis due to calcium oxalate consists of surgical removal of stones, control of the diet to restrict calcium or oxalate, and ingestion of large quantities of water to dilute the urine. Attempts at chemotherapy have included the administration of magnesium oxide, calcium carbimide, orthophosphate, cellulose phosphate, isocarboxazide, thiazide diuretics, allopurinol and succinimide. Limited success has been realized by these drug approaches. No drug which specifically inhibits the biosynthetic formation of oxalic acid has previously been developed for the treatment of renal lithiasis.

The immediate metabolic precursor of the majority of the oxalate in the urine of a typical patient is glyoxylic acid. In turn its most important precursor is glycolic acid. The enzyme glycolate oxidase is able to carry out the oxidation of glycolic acid, through glyoxylic acid, to oxalic acid. Inhibition of this enzyme will, therefore, reduce the concentration of oxalic acid in the kidney and bladder, decreasing the probability that calcium oxalate crystallization will occur. Thus inhibitors of glycolate oxidase provide a specific approach to the prevention and treatment of calcium oxalate renal lithiasis.

Liao, et al, *Arch. Biochem. Biophys.*, 154, 68–75 (1973) have shown that phenyllactic acid and n-heptanoic acid, which are inhibitors of glycolate oxidase, inhibit oxalate biosynthesis in isolated perfused rat liver. These compounds are not sufficiently potent to be useful as drugs.

The preparation of 3-hydroxy-4-phenyl-3-pyrroline-2,5-dione

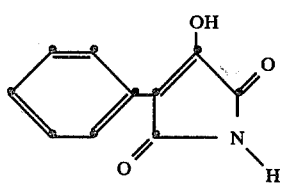

has been described by Harlay, *J. Pharm.Chim.*, 24, 537-48 (1936). 3-Hydroxy-4-aryl-3-pyrroline-2,5-diones are described in U.S. Pat. No. 3,349,263 as intermediates in the preparation of antiphlogistic substances.

A number of 3-hydroxy-4-substitutedphenyl-3-pyrroline-2,5-diones are reported by G. S. Skinner, et al., J. Am. Chem. Soc., 73, 2230 (1951). (In this paper these compounds are referred to as pyrrolidine-2,3,5-trione derivatives). 3-Hydroxy-4-(4-bromo-1-naphthyl)-3-pyrroline-2,5-dione is described by G. S. Skinner, et al., J. Am. Chem. Soc., 70, 4011 (1948).

SUMMARY OF THE INVENTION

It has now been found that novel compounds of the formula:

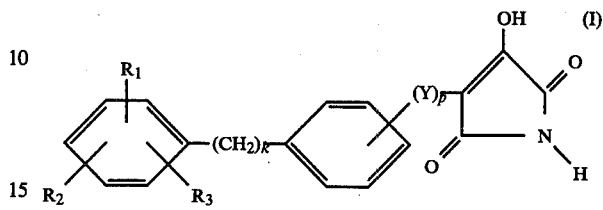

wherein
Y is $(CH_2)_n$: $(CH_2)_m$—O: $(CH_2)_m$—S:
n is 0 to 3;
m is 0 to 2:
k is 0 to 3:
p is 0 or 1:
$R_1$, $R_2$ and $R_3$ are independently hydrogen, halogen, loweralkyl containing 1 to 6 carbon atoms, loweralkoxy containing 1 to 6 carbon atoms.
wherein
the attachment of

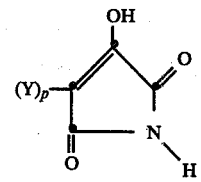

to the aromatic ring is restricted to positions para or meta to the other substituent or pharmaceutically acceptabls salts thereof are potent inhibitors of glycolate oxidase. They are, therefore, useful in the treatment and prevention of calcium oxalate kidney and bladder stone disease.

Further preferred compounds of the present invention are those
wherein
p=0 having the structure:

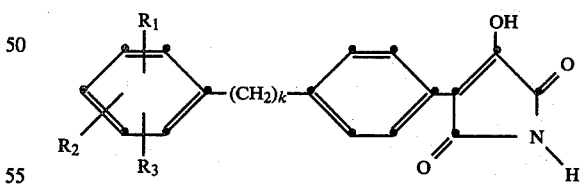

and

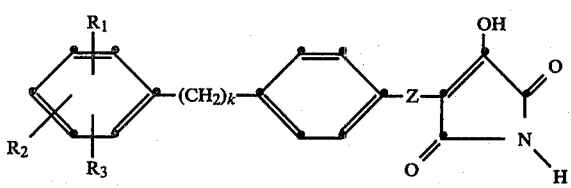

wherein
Z is O, S;
k, $R_1$, $R_2$ and $R_3$ are as defined above.

DETAILED DESCRIPTION

About 70% of all renal calculi contain oxalate as the main component of the matrix. In the majority of patients the condition is associated with a higher than average level of metabolically produced oxalate. The major pathway for biosynthesis of oxalate can be represented as follows:

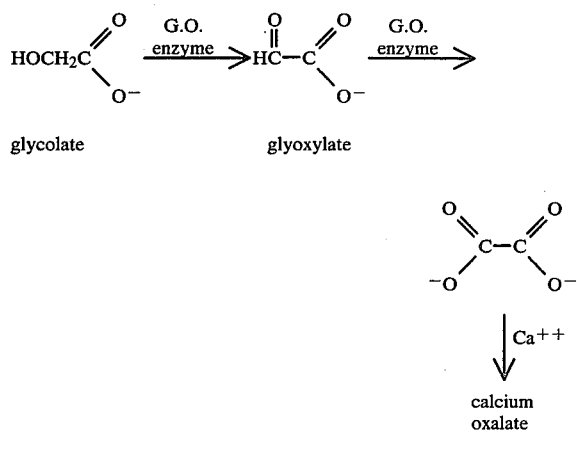

Glyoxylate is the major immediate forerunner of oxalate. An inhibitor of glycolate oxidase (G.O.) will inhibit both the conversion of glyoxylate to oxalate as well as the production of glyoxylate from glycolate. By reducing oxalic acid levels in the urine with the compounds of this invention, the formation of oxalate calculi will be reduced or prevented.

Compounds of formula (I) are potent inhibitors of glycolate oxidase and thus are useful in restricting oxalate levels in the kidney and urine. Further, they are useful in the treatment and prevention of renal disease due to calcium oxalate stone formation in the kidney and bladder. They also may be useful in the treatment of the genetically inherited diseases termed Hyperoxaluria types I and II in which very high levels of metabolic oxalate are present.

Compounds of formula (I) have been unexpectedly found to block the contractions of guinea pig ileum induced by Slow Reacting Substance of Anaphylaxis (SRS-A). They are ineffective against contractions caused by histamine, which demonstrates specificity against SRS-A. SRA-A is considered a major mediator in human allergic asthma. Thus the compounds of formula (I) are useful in the treatment of allergy, especially allergic asthma.

Compounds of formula (I) can be prepared according to the following general routes:

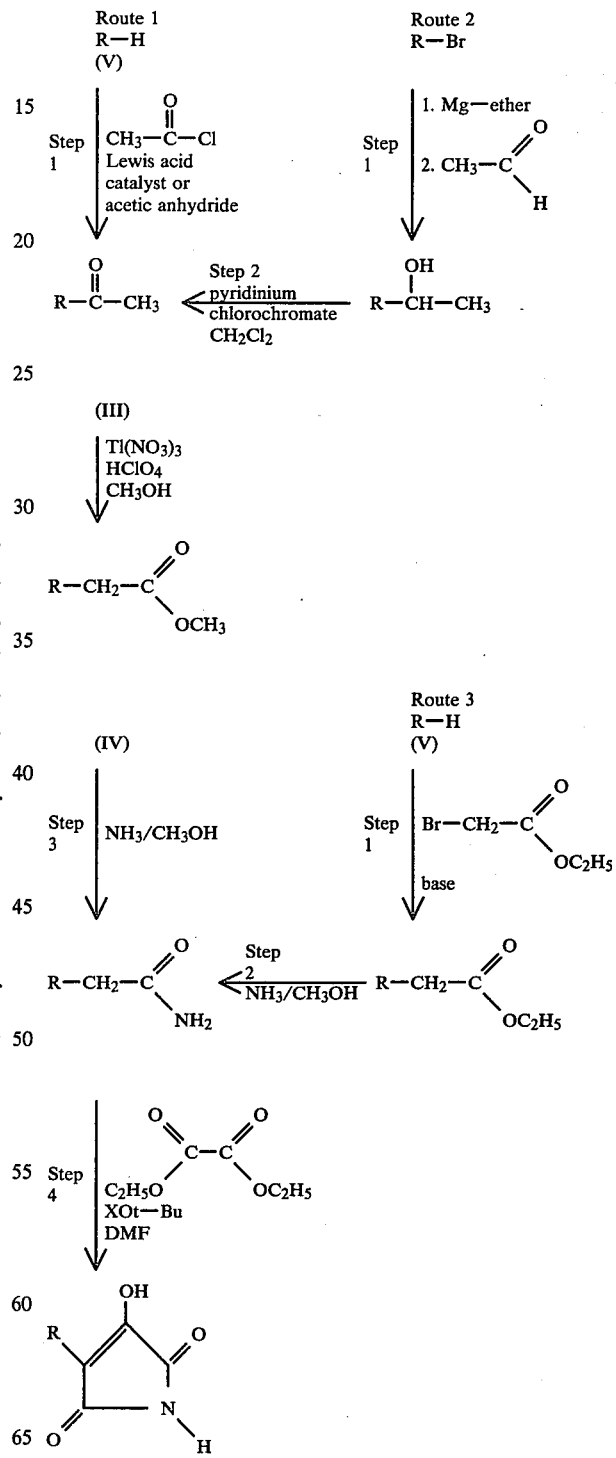

General Routes

-continued
General Routes

Route 4
R'—(CH$_2$)$_{n+1}$—CN

Step 1 | Base (COOC$_2$H$_5$)$_2$

R'—(CH$_2$)$_n$—CH—CN
         |
         COCOOC$_2$H$_5$

| C$_2$H$_5$OH/HCl

R'—(CH$_2$)$_n$—CH—C=NH·HCl
         |      |
         OC$_2$H$_5$
         COCOOC$_2$H$_5$

| Δ
  CHCl$_3$

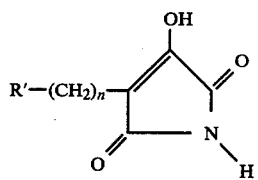

1. H$_2$SO$_4$ or CH$_3$SO$_3$H

2. C$_2$H$_5$OH—H$_2$O wherein R and R'-(CH$_2$)$_n$— represent substituents at the 4-position of the 3-hydroxy-3-pyrroline-2,5-dione in formula (I) above.

Route 1 is applicable when p in formula (I) above is 0, and the 3-hydroxy-3-pyrroline-2,5-dione moiety is para to the second substituent on the benzene ring. Route 2 is applicable to the synthesis of derivatives in which the 3-hydroxy-3-pyrroline-2,5-dione moiety is attached para or meta to the second substituent on the benzene ring, and in which p in formula (I) is also 0. Route 3 is applicable when Y in formula (I) above is (CH$_2$)$_m$—O or (CH$_2$)$_m$—S. Route 4 is the most generally applicable and is the preferred route in the case when Y in formula (I) above is (CH$_2$)$_n$ and n is 1 to 3. It is also applicable when n is 0.

The following examples, given by way of illustration and not to be construed as limiting, further clarify the invention.

General Procedure for the Preparation of Phenyl-Substituted Acetophenones

Route 1, Step 1

The methyl ketones (III) are prepared by acetylation of the parent compound (V) with acetyl chloride or acetic anhydride and a Lewis acid catalyst under conventional Friedel Craft conditions.

Examples of methyl ketones (III) prepared by this process are set forth in Table 1 below:

TABLE I

| Compound (III) | Catalyst Solvent | Yield % | MP °C. Solvent | Analysis | | |
|---|---|---|---|---|---|---|
| 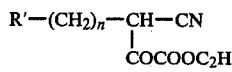 4-(4-bromophenyl)-acetophenone | AlCl$_3$ CH$_2$Cl$_2$ | 61 | 126–128 petroleum ether/ benzene | | | |
| | | | | | Required | Found |
| 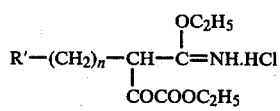 4-(3,4-dichlorobenzyl)-acetophenone | AlCl$_3$ CH$_2$Cl$_2$ | 75 | 37.5–39 diisopropyl ether/petroleum ether | C H Cl | 64.53 4.33 25.39 | 64.52 4.41 25.12 |

General Procedure for the Preparation of Methyl Substituted Arylacetates (IV)

Route 1, Step 2

Substituted arylacetic acid esters (IV), were made by the oxidative rearrangement of the corresponding methyl ketones (III) using the method of E. C. Taylor and A. McKillop, J. Amer. Chem. Soc., 93, 4919 (1971), ibid 95, 3340 (1973). Examples of substituted arylacetic acid esters (IV) prepared by this process are set forth in Table II below.

TABLE II

| Compound (IV) | Yield % | MP °C. Solvent | Formula | Analysis | | |
|---|---|---|---|---|---|---|
| | | | | | Required | Found |
| Br—⟨⟩—⟨⟩—CH$_2$COOMe methyl 4-(4-bromophenyl)-phenylacetate | 99 (crude) | 58–60 di-iso-propyl ether | C$_{15}$H$_{13}$BrO$_2$ | C H Br | 59.03 4.29 26.18 | 59.15 4.25 26.32 |
| Cl—⟨⟩—CH$_2$—⟨⟩—CH$_2$COOMe (with Cl) methyl 4-(3,4-dichlorobenzyl)phenylacetate | 100 (crude) | 41–43 short path distillation | C$_{16}$H$_{14}$Cl$_2$O$_2$ | C H Cl | 62.15 4.56 22.93 | 62.04 4.42 23.77 |

General Procedure for Preparing the Substituted Acetamides

Route 1, Step 3

The substituted acetic acid esters (IV) were converted to the corresponding amides (VII) by treatment with 7½ parts volume by weight of a saturated solution of ammonia in methanol at room temperature. Conversion to the amide was followed by thin layer chromatography. Examples of substituted acetamides (VII) prepared by this process are set forth in Table III below.

General Method for the Preparation of 3-Hydroxy-4-substituted-3-pyrroline-2,5-diones

Routes 1,2 and 3, Step 4

A mixture of the substituted acetamide (10 mmole), diethyl oxalate (1.533 g, 10.5 mmole) and dry dimethylformamide (20 ml) is stirred under nitrogen or argon and cooled in an ice-bath. Potassium t-butoxide (2.464 g, 22 mmole) is added in two equal portions 15 minutes apart and the reaction mixture is stirred for about 30 minutes in the ice-bath and then at room temperature overnight. The reaction mixture is poured into ice-

TABLE III

| Compound (VII) | Yield % | MP °C. Solvent | Formula | Analysis Required | Analysis Found |
|---|---|---|---|---|---|
| $C_6H_5$-⟨⟩-⟨⟩-$CH_2$-C(=O)-$NH_2$<br>4-biphenyl-acetamide | 68 | 250–252<br>acetone | | | |
| Br-⟨⟩-⟨⟩-$CH_2$-C(=O)-$NH_2$<br>4'-bromo-4-biphenylyl-acetamide | 50 | 265–267<br>DMF/MeCN | $C_{14}H_{12}BrNO$ | C 57.95<br>H 4.17<br>Br 27.54<br>N 4.82 | 57.51<br>4.70<br>27.46<br>4.93 |
| Cl-⟨⟩(Cl)-$CH_2$-⟨⟩-$CH_2$-C(=O)-$NH_2$<br>4-(3,4-dichlorobenzyl)-phenylacetamide | 42 | 151–153<br>$C_6H_6$ | $C_{15}H_{13}Cl_2NO$ | C 61.24<br>H 4.45<br>Cl 24.10<br>N 4.71 | 60.80<br>4.87<br>24.16<br>4.87 |
| $C_6H_5$-⟨⟩-⟨⟩-O-$CH_2$-C(=O)-$NH_2$<br>4-biphenylyloxy-acetamide | 67 overall | 192–193 | $C_{14}H_{13}NO_2$ | C 73.99<br>H 5.76<br>N 6.16 | 73.58<br>6.05<br>6.04 |
| $C_6H_5$-⟨⟩-⟨⟩-S-$CH_2$-C(=O)-$NH_2$<br>4-biphenylylthio-acetamide | 86 | 188.5–189.6 | $C_{14}H_{13}NOS$ | C 69.11<br>H 5.39<br>S 13.18 | 68.68<br>5.84<br>12.97 |

The last two compounds in Table III above were prepared by Route 3 of the General Routes. Route 3 of the General Routes is applicable when Y is $(CH_2)_m$—O or $(CH_2)_m$—S in formula (I) above.

General Procedure for the Prepartion of Esters of Substituted Phenyl-thioacetic and -oxyacetic Acids (VI)

Route 3, Step 1

The corresponding substituted phenol or thiophenol (10 mmole) is added to a solution of sodium (10 mmole) in ethanol (20 ml) under nitrogen. To the cooled mixture is added ethyl bromoacetate (10 mmole) in ethanol (10 ml), and then the mixture is stirred for an appropriate time at room temperature in order to complete the reaction. The ester (VI) is isolated by addition of water and extraction with methylene chloride. The crude ester is used for the preparation of the corresponding amide (VII) without further purification.

In the case wherein m is 1 or 2 in formula (I) above, NaH in DMF or THF in place of sodium and ethanol is used to form the anion before adding ethyl bromoacetate in the same solvent.

water (100 ml). If the potassium salt of the product dissolves, the aqueous mixture is extracted with ethyl acetate (2×35 ml) and then acidified with 6N hydrochloric acid in order to precipitate the product. The product is either collected by filtration or by extraction with ethyl acetate.

If the potassium salt is not soluble when the reaction mixture is quenched in ice-water, then it is necessary to acidify the resulting suspension and collect the product by filtration. The crude product is generally less pure when obtained in this way.

The compounds may be solvated after recrystallization (with either DMF, dioxane, isopropanol or acetonitrile) and require drying at 110° C./0.05 Torr in order to remove the solvate. Examples of 3-hydroxy-4-substituted-3-pyrroline-2,5-diones prepared by this process are set forth in Table IV below.

When the starting materials for Route 1, Step 1 are 3-chloro-4-methoxybiphenyl, 2,5-dichloro-4-methoxybiphenyl, 2-chloro-5-methylbiphenyl and 4-chloro-2-methylbiphenyl, and Steps 1, 2, 3, and 4 are followed, there are obtained 4-(3'-chloro-4'-methoxy-4-biphenylyl)-3-hydroxy-3-pyrroline-2,5-dione, 4-(2',5'- dichloro-4'-methoxy-4-biphenylyl)-3-hydroxy-3-pyrroline-2,5-dione, 4-(2'-chloro-5'-methyl-4-biphenylyl)-3-hydroxy-3-pyrroline-2,5-dione and 4-(4'-chloro-2'-methyl-4-biphenyly)-3-hydroxy-3-pyrroline-2,5-dione, respectively. When 1-chloro-4-(2-phenylethyl)benzene is utilized as starting material in Route 1, Step 1 and the product submitted to Steps 2, 3, and 4, there is obtained 4-{4-[2-(4-chlorophenyl)ethyl]phenyl}-3-hydroxy-3-pyrroline-2,5-dione. When 4'-methoxy-4-biphenyl-ylacetic acid ethyl ester is the starting material for Route 1, Step 3, there is obtained after Step 4, 4-(4'-methoxy-4-biphenylyl)-3-hydroxy-3-pyrroline-2,5-dione. When 3-acetylbiphenyl is subjected to steps 2,3 and 4 of Route 1 there is obtained 3-hydroxy-4-(3-biphenyl)-3-pyrroline-2,5-dione. When 3-hydroxy-biphenyl and 3-mercaptobiphenyl are the starting materials for Route 3, Step 1, and Steps 1 and 2 of Route 3 and Step 4 of Route 1 are followed, there are obtained 3-hydroxy-4-[3-biphenylyl)oxy)]-3-pyrroline-2,5-dione, and 3-hydroxy-4-[(3-biphenylyl)thio)]-3-pyrroline-2,5-dione, respectively. When 4'-chloro-3-hydroxybiphenyl is the starting material for Route 3, and Steps 1 and 2, Route 3, and Step 4, Route 1, are followed there is obtained 3-hydroxy-4-[(4'-chloro-3-biphenylyl)oxy]-3-pyrroline-2,5-dione.

General Method for the Preparation of Acetophenone Intermediates by the Grignard Procedure, Followed by Oxidation (Route 2, Steps 1 and 2)

The bromophenyl starting material (10 mmole) is reacted with dry magnesium (12 mmole) in 50 ml dry diethyl ether according to standard procedures for preparing Grignard intermediates. To the Grignard solution at 0° C. is added an ether solution of acetaldehyde (11 mmole) at 0° C. After warming to room temperature, the material is hydrolyzed by the addition of ice-cold aqueous ammonium chloride solution. The ether solution is washed with water, dried and evaporated to give crude methyl carbinol intermediate which is purified by vacuum distillation of chromatography on silica gel. The methyl carbinol is oxidized to the ketone with pyridinium chlorochoromate in inert solvent, such as methylene chloride, using the procedure E. J. Corey and J. W. Suggs, Tetrahedron Letters, 2647 (1975).

TABLE IV

| Compound (I) | Yield % | MP °C. Solvent | Formula | Analysis | | |
|---|---|---|---|---|---|---|
| | | | | | Required | Found |
| 4-(4-biphenylyl)-3-hydroxy-3-pyrroline-2,5-dione | 62 | 305–307 dec. DMF/MeCN | $C_{16}H_{11}NO_3$ | C<br>H<br>N | 72.44<br>4.18<br>5.28 | 72.44<br>4.60<br>5.33 |
| 4-(4'-bromo-4-biphenylyl)-3-hydroxy-3-pyrroline-2,5-dione | 50 | 326–328 dec. DMF/MeCN | $C_{16}H_{10}BrNO_3$ | C<br>H<br>N | 55.83<br>2.93<br>4.07 | 55.84<br>2.98<br>3.86 |
| 4-[4-(3,4-dichlorobenzyl)phenyl]-3-hydroxy-3-pyrroline-2,5-dione | 54 | 234–236 MeCN | $C_{17}H_{11}Cl_2NO_3$ | C<br>H<br>N | 58.64<br>3.17<br>4.02 | 58.72<br>3.22<br>4.00 |
| 4-(4-biphenylyloxy)-3-hydroxy-3-pyrroline-2,5-dione | 48 | 247–248 dec. isopropanol | $C_{16}H_{11}NO_4$ | C<br>H<br>N | 68.32<br>3.94<br>4.98 | 68.62<br>4.08<br>4.83 |

TABLE IV-continued

| Compound (I) | Yield % | MP °C. Solvent | Formula | Analysis Required | Found |
|---|---|---|---|---|---|
| 4-(4-biphenylylthio)-3-hydroxy-3-pyrroline-2,5-dione | 63 | dec. >220 isopropanol | $C_{16}H_{11}NO_3S$ | C 64.63<br>H 3.73<br>S 10.78 | 64.37<br>3.85<br>11.09 |

Note:
The compounds of this invention may also be designated 3-substituted-4-hydroxy-3-pyrroline-2,5-dione derivatives.

In the case of Route 4, the phenylalkylnitrile is reacted with diethyl oxalate in an alcohol such as methanol, ethanol, isopropanol and the like, in the presence of strong base, such as the corresponding sodium or potassium alkoxides. Formation of the anion adjacent to the nitrile group is necessary for reaction to take place. The reaction can be carried out in aprotic solvents such as dimethylformamide using a strong base, such as sodium and potassium alkoxides, lithium diisopropylamide and the like. The temperature for the reaction can range from 0°–100° C.

The resulting ester nitrile is treated with ethanol saturated with anhydrous hydrogen chloride to give the imino ether. The solvent is evaporated and the residue heated with chloroform to yield the desired 3-hydroxy-3-pyrroliine-2,5-dione.

Alternately, the ester nitrile may be dissolved in sulfuric acid or methanesulfonic acid and quenched in ice-water according to the procedure set forth in J. Klosa, Chem. Ber., 85, 229 (1952); U.S. Pat. No. 3,349,263 and Harlay et al., J. Pharm. Chim., 24, 537–48 (1936).

For compounds where $(Y)_p$ is $(CH_2)_n$ and n=1–3, the required nitrile intermediates can be obtained readily starting from the correspond arylacetic acid ester derivatives by standard chain extension reactions well known in the art. Thus the arylacetic ester intermediate can be reduced with lithium aluminum hydride to the 2-aryl-1-ethanol. Conversion of the ethanol intermediate to the corresponding halide (chloride or bromide) is accomplished with halogenating agents such as phosphorus oxychloride, thionyl chloride, carbon tetrachloride-triphenylphosphine, or phosphorus oxybromide. Reaction of the halide intermediate with cyanide ion provides the next higher homologous nitrile. In some instances it is preferable to convert the ethanol intermediate to the p-toluenesulfonate ester, using p-toluenesulfonyl chloride in pyridine. Displacement of the p-toluenesulfonate group by cyanide ion then provides the homologous nitrile. For further stepwise homologation the nitrile derivative is hydrolyzed to the corresponding carboxylic acid, employing aqueous mineral acid or base. The resulting acid, or its methyl or ethyl ester, is reduced to the corresponding alcohol with diborane, or lithium aluminum hydride respectively. The above sequence of halogenation, or p-toluenesulfonate ester formation followed by displacement of the leaving group with cyanide ion, is then repeated.

Included within the scope of the invention are the pharmaceutically acceptable salts of formula (I) compounds. The compounds of formula (I) are strong organic acids with a pKa in the range 2–6. Thus salts are readily formed with the usual inorganic cations such as sodium, potassium and ammonium. Salts with organic amines such as trimethylamine, triethylamine, n-butylamine and the like are also very stable. The neutralization can be carried out by a variety of procedures known to the art to be generally useful for the preparation of such salts. The choice of the most suitable procedure will depend on a variety of factors including convenience of operation, economic considerations, and particularly the solubility characteristics of the particular free base, the acid, and the acid addition salt.

The compounds of formula (I) are utilized for the utilities stated by formulating them in a composition such as tablet, capsule or elixir for oral administration. Sterile solutions or suspensions can be used for parenteral administration. About 10 to 200 mg of a compound of formula (I) or a physiologically able salt is compounded with a physiologically acceptable vehicle, carrier, excipient, binder, preservative, stabilizer, flavor, etc., in a unit dosage form as called for by accepted pharmaceutical practice. The amount of active substance in the composition is such that dosage in the range indicated is obtained. The total daily dose is in the 30 to 2000 mg range and preferably in the 50 to 1000 mg. range.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose, or saccharin; a flavoring agent such as peppermint, oil of wintergreen or cherry. When the dosage unit form is a capsule, it may contain in addition to materials of the above type a liquid carrier such as a fatty oil. Various other materials may be present as coating or to otherwise enhance the pharmaceutical elegance of the preparation. For instance, tablets may be coated with shellac, sugar or the like. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a conventional vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

What is claimed is:

1. The compounds having the structure:

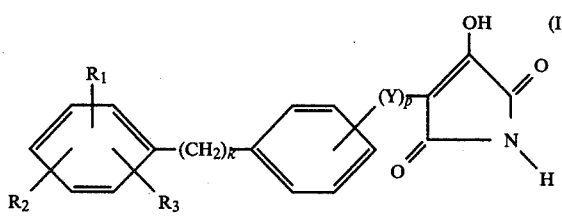

wherein
Y is $(CH_2)_n$; $(CH_2)_m$—O; $(CH_2)_m$—S;
n is 1 to 3;
m is 0 to 2;
k is 0 to 3;
p is 1;
$R_1$, $R_2$ and $R_3$ are independently hydrogen, halogen, loweralkyl containing 1 to 6 carbon atoms, loweralkoxy containing 1 to 6 carbon atoms,
wherein
the attachment of

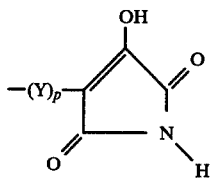

to the aromatic ring is restricted to positions para or meta to the other substituent or pharmaceutically acceptable salts thereof.

2. The compounds according to claim 1 having the structure:

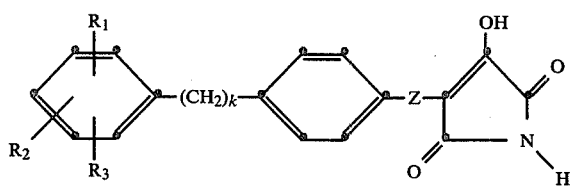

wherein
Z is O, S;
k is 0 to 3;
$R_1$, $R_2$ and $R_3$ are independently hydrogen, halogen, loweralkyl containing 1 to 6 carbon atoms, loweralkoxy containing 1 to 6 carbon atoms.

3. A compound according to claim 2 designated 4-(4-biphenylyloxy)-3-hydroxy-3-pyrroline-2,5-dione.

4. A pharmaceutical composition for preventing or treating calcium oxalate renal lithiasis comprising an effective amount of a compound of claim 1 or the pharmaceutically acceptable salts thereof and a pharmaceutically acceptable carrier thereof.

5. A method of treating persons afflicted with calcium oxalate kidney or bladder stones or preventing the formation of calcium oxalate kidney or bladder stones which comprises administering to such a patient an effective amount of a compound of claim 1.

* * * * *